United States Patent
Perlhagen et al.

(10) Patent No.: US 7,160,256 B2
(45) Date of Patent: Jan. 9, 2007

(54) DEVICE FOR COLLECTION OF UNCONTAMINATED URINE FROM CHILDREN

(76) Inventors: Markus Perlhagen, Lindahls väg 9, S-260, 83 Vejbystrand (SE); Roger Jönsson, Viktorrydbergsgatan 48-1, S-412 81, Göteborg (SE)

(*) Notice: Subject to any disclaimer, the term of this patent is extended or adjusted under 35 U.S.C. 154(b) by 172 days.

(21) Appl. No.: 10/522,508

(22) PCT Filed: Jul. 24, 2003

(86) PCT No.: PCT/SE03/01238

§ 371 (c)(1),
(2), (4) Date: Jan. 26, 2005

(87) PCT Pub. No.: WO2004/021890

PCT Pub. Date: Mar. 18, 2004

(65) Prior Publication Data
US 2005/0240164 A1 Oct. 27, 2005

(30) Foreign Application Priority Data
Jul. 29, 2002 (SE) .................................. 02023307

(51) Int. Cl.
*A61B 5/00* (2006.01)
*B65D 33/00* (2006.01)
*B65D 81/00* (2006.01)

(52) U.S. Cl. .................................................... 600/580

(58) Field of Classification Search ........ 600/573–575, 600/580, 584; 604/347, 348, 350, 352, 354, 604/346, 317, 361, 322, 327, 329; 4/144.2, 4/144.3; 436/174; 128/DIG. 24; 206/219; 422/102, 944

See application file for complete search history.

(56) References Cited

U.S. PATENT DOCUMENTS

| | | | | |
|---|---|---|---|---|
| 2,877,769 A | * | 3/1959 | Hill | 604/347 |
| 3,200,415 A | * | 8/1965 | Breece, Jr. | 4/144.2 |
| 3,295,145 A | * | 1/1967 | Ericson | 4/144.3 |
| 3,340,876 A | * | 9/1967 | Hill | 600/580 |
| 3,368,561 A | * | 2/1968 | Ericson et al. | 604/347 |
| 3,406,690 A | * | 10/1968 | Igel et al. | 600/580 |
| 3,523,537 A | * | 8/1970 | Hill | 600/574 |
| 3,660,033 A | * | 5/1972 | Schwartz | 436/174 |
| 3,918,433 A | * | 11/1975 | Fuisz | 600/573 |
| 4,203,169 A | | 5/1980 | Dale | |
| 4,557,274 A | | 12/1985 | Cawood | |
| 4,804,377 A | * | 2/1989 | Hanifl et al. | 604/352 |
| 4,911,698 A | * | 3/1990 | Wapner | 604/329 |
| 6,375,643 B1 | * | 4/2002 | Moorhead et al. | 604/322 |

* cited by examiner

*Primary Examiner*—Max F. Hindenburg
*Assistant Examiner*—Brian Szmal
(74) *Attorney, Agent, or Firm*—Larson & Larson, PA; Herbert W. Larson

(57) ABSTRACT

A disposable device for collection of uncontaminated urine samples from small children comprising a sterile container with an inlet that eliminates direct contact between the wearers skin and the inside of the container, and which is initially closed by a delaying mechanism consisting of, e.g. a water soluble adhesive substance or material. The flow to the container is initially hindered by the delaying mechanism located in the inlet of the container. This causes the initial portion of fluid, which may be contaminated with bacteria, to be absorbed by an absorbing layer whereafter the inlet is automatically opened so that the remaining fluid can reach the container essentially uncontaminated.

8 Claims, 4 Drawing Sheets

DEVICE FOR COLLECTION OF UNCONTAMINATED URINE FROM CHILDREN

PRIOR APPLICATIONS

This §371 National Phase patent application bases priority on International Application No. PCT/SE2003/001238, filed on Jul. 24, 2003, which in turn bases priority on Swedish Application No. SE 0202330-7, filed on Jul. 29, 2002.

BACKGROUND OF THE INVENTION

1. Field of the Invention

The present invention relates to a device used for collection of uncontaminated urine samples from small children.

2. Description of the Prior Art

Infection of the urinary tract is a relatively common and potentially serious disease, especially in children. Urinary tract infection is diagnosed by demonstrating growth of bacteria in the urine. Crucial for the reliability of such analysis is that the enteric bacteria that normally colonize the skin of the uro genital area do not contaminate the urine sample. The most reliable ways to obtain an uncontaminated urine sample is by percutaneous bladder tap, urethral catheterization or by midstream specimen. These methods are, however, in many cases not suitable. Percutaneous bladder taps, as well as urethral catheterization, are proportionately traumatic procedures and midstream specimens are for practical reasons difficult to obtain, above all from small children since they usually are not able to produce a urine sample on demand. Ordinarily, a collecting bag attached to the genital area is therefore used. This allows the children to move around and does not imply any significant discomfort to them.

The collecting devices that are currently used are designed as a plastic bag. It has an opening on one side that is attached to the genital area with an adhesive material.

Examples of such devices can be found in patents GB 1051875, WO 0000111, SE 333792, U.S. Pat. No. 3,406,690, U.S. Pat. No. 3,523,537, and U.S. Pat. No. 3,200,415. Alternative designs are presented in U.S. Pat. No. 3,918,433 and GB 2163656. Common to the mentioned patents is, however, that they mainly focus on the attachment and collection functions of the device and that they do not address the risk of contamination. sufficiently. Other patents that address this problem can be found in U.S. Pat. No. 4,557,274, U.S. Pat. No. 4,492,258, and U.S. Pat. No. 3,881,465.

Using the above mentioned devices, a substantial part of the samples is rendered useless and has to be resampled since they have been contaminated with non-relevant bacteria. This leads to delay and difficulties in diagnosing and treatment, yielding over, as well as under, diagnosing the consequences, being apart from higher costs and ineffective use of medical care resources, unnecessary suffering for the patients and their parents.

SUMMARY OF THE INVENTION

The purpose of the invention is to mainly create a disposable device that solves the problem with bacterial contamination when collecting urine samples from children. The device should furthermore be easy to use and be manufacturable at a cost that does not substantially exceed the manufacturing cost of the products used today.

When using conventional devices, the main contamination occurs when the fluid on its way to the container collects non-relevant bacteria, partly directly from the skin, partly from those parts of the collecting device that have been in direct contact with it.

In order to avoid this, the present invention is furnished with a collecting bag whose opening excludes all direct contact between the skin and the inner face of the collecting bag. The opening is, furthermore, initially sealed with, for example, a water soluble adhesive material or substance. In the moment of voiding, this is dissolved by the fluid so that the inlet of the collecting bag opens. The fluid that initially is prevented from reaching the collecting bag is almost instantly absorbed by the absorbing material.

This design renders a rinsing effect of those surfaces that the initial fluid is exposed to, simultaneously preventing non-relevant bacteria being flushed along from reaching the collecting bag.

BRIEF DESCRIPTION OF THE DRAWINGS

Further advantages and features of the present invention can be gathered from the following description of the preferred embodiment relative to the attached drawings, wherein.

DETAILED DESCRIPTION OF THE PREFERRED EMBODIMENT

Figure 1:
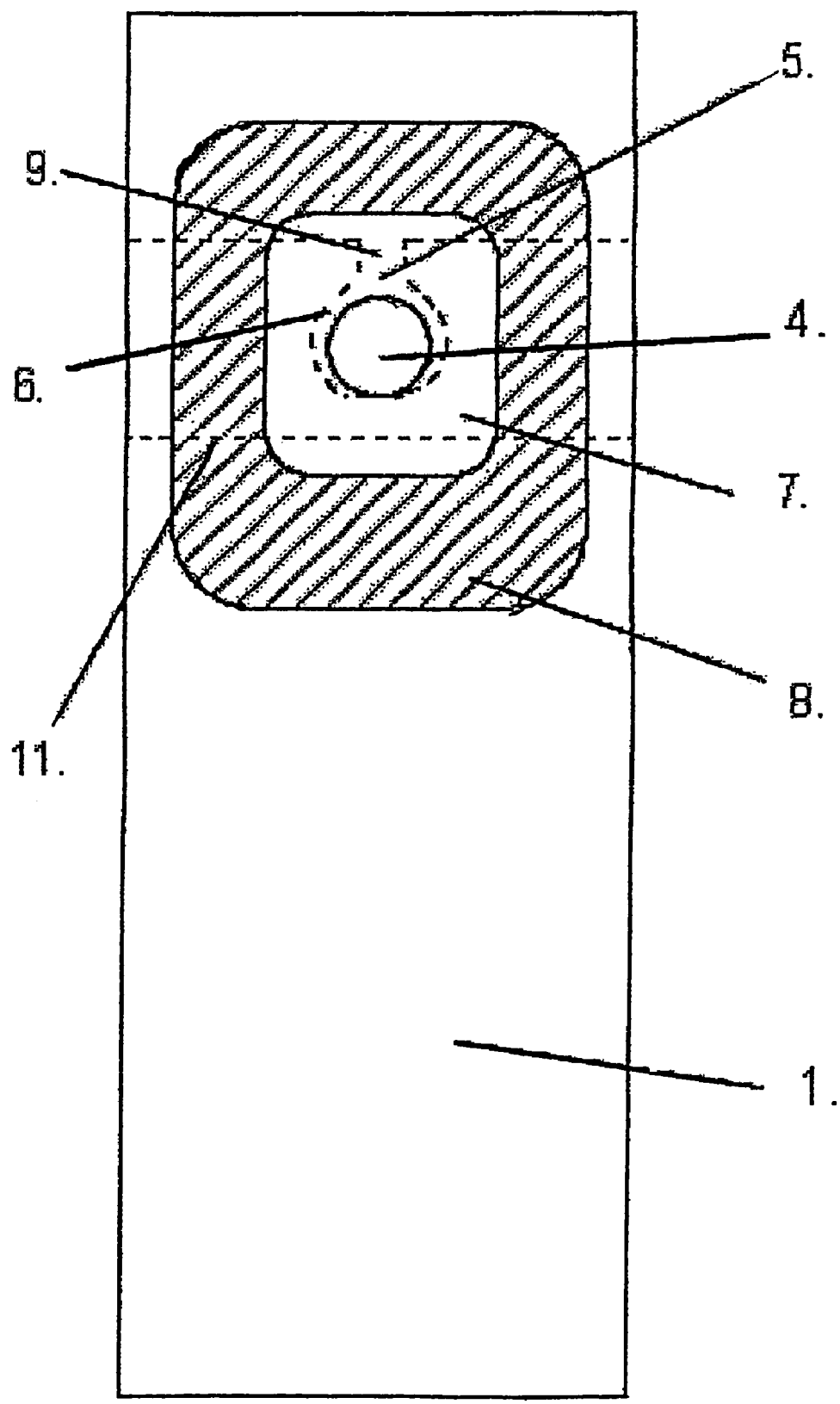
FIG. 1 is a front perspective view of a first embodiment of the device for collection of uncontaminated urine from a child.

All figures and descriptions relate to the user point of view. The expression "from above" means consequently the side the user sees from above, that is the side that, when in use, is attached to the body.

The expression "uncontaminated" here means a contamination with bacteria that is significantly below the lower value for significant bacteriuria applied to this kind of urine analysis.

The invention consists of a collection bag 1 with an absorbing material 7 placed around an opening 4 on the upper face of the device. The device is worn with the absorbing layer 7 against the body, placed so that said opening 4 is situated opposite to the urethral opening. Fluid reaches the collecting bag 1 via said opening 4, whereafter it passes a tube-shaped channel 5 initially closed by a delay mechanism 9 consisting of, for example, a water soluble adhesive material or substance 9. When the urine reaches said opening 4, instant flow to the collecting bag 1 is prevented due to the adhesive substance 9 placed in the channel 5, whereby the fluid is absorbed by the absorbing material along with a major part of the bacteria that have contaminated the transport route of the fluid. Thereafter, the adhesive substance 9 is dissolved so that said channel 5 is opened, whereafter the remaining fluid is able to reach the collecting bag 1, mainly uncontaminated.

Figure 2:
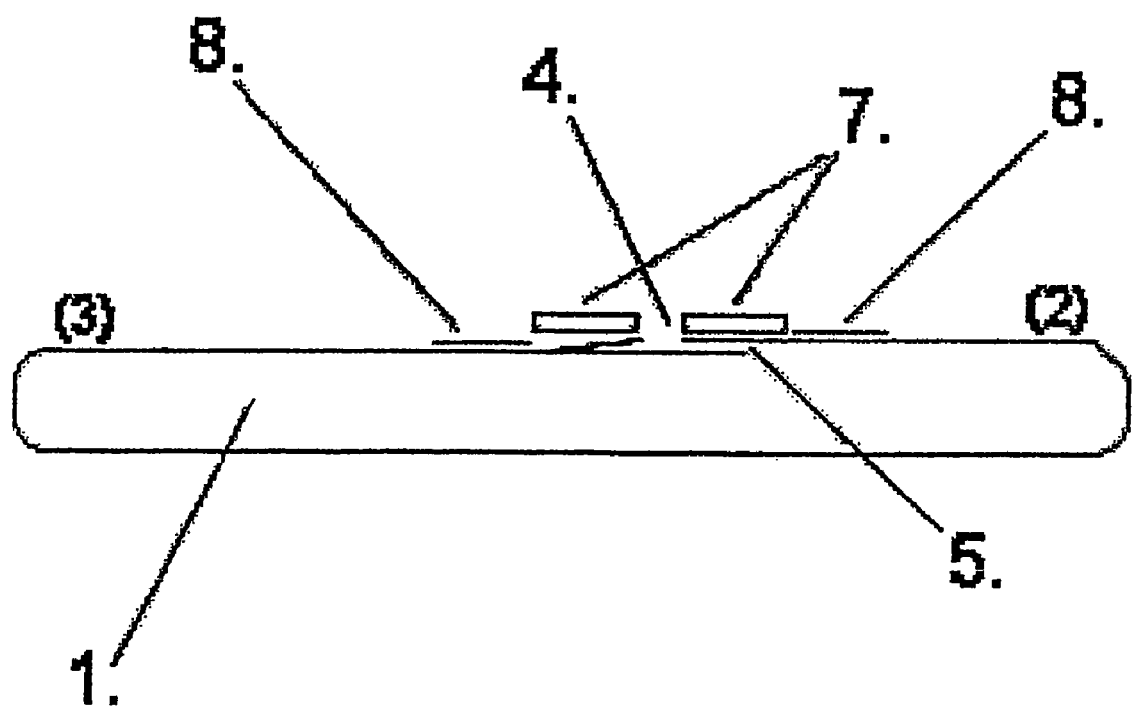
FIG. 2 is a side view of the embodiment shown in FIG. 1.
Figure 3:
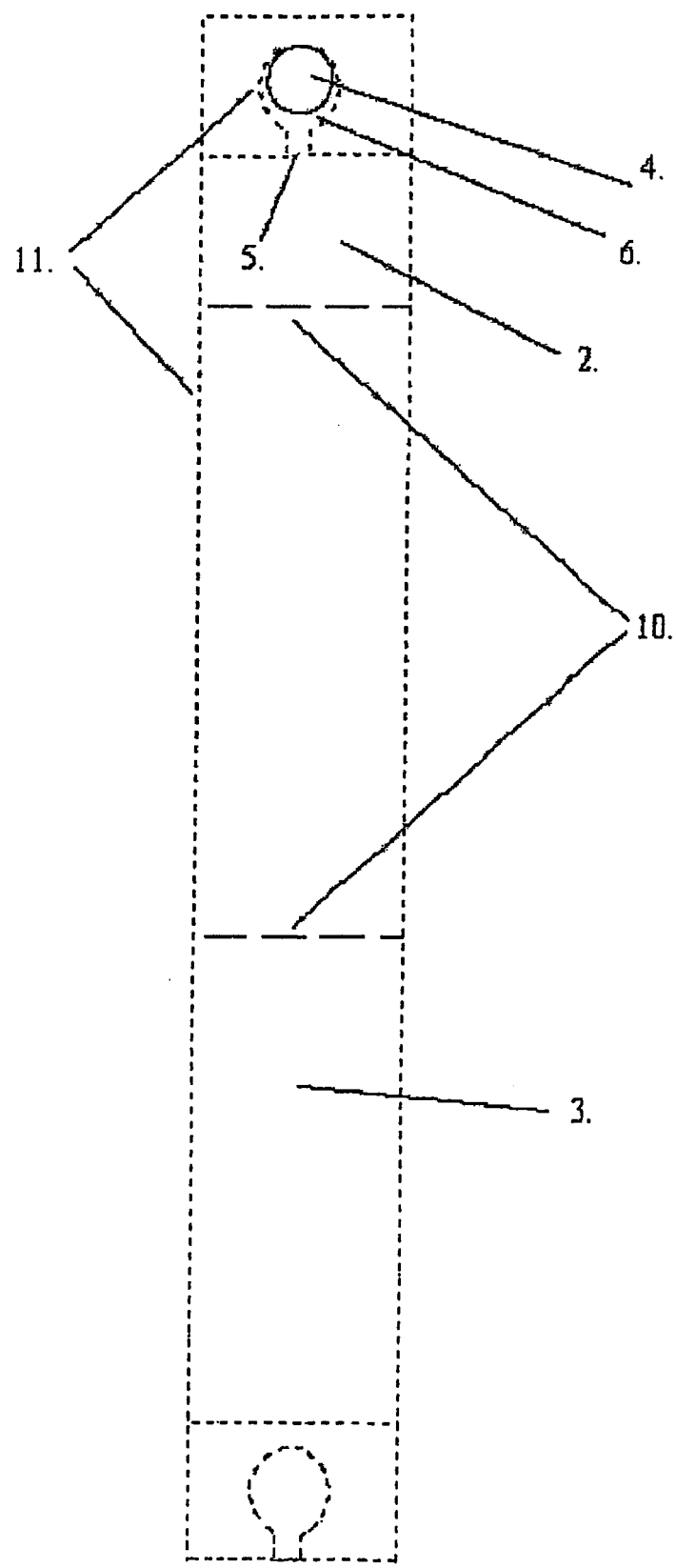
FIG. 3 shows the embodiment of FIG. 1 in an unfolded position prior to welding.

According to the first embodiment shown in FIGS. 1–3, the device is shaped as a bag similar to the bags used today. According to said suggestion, it can be manufactured from a single piece of plastic sheet material (see FIG. 3). When the opening 4 has been made and the delay mechanism 9 has been positioned on its intended place, the work piece is folded in two places 10 and welded together 11, according to FIG. 3. Thereafter, the absorbing layer 7 and the adhesive surface 8 is mounted.

Figure 4:
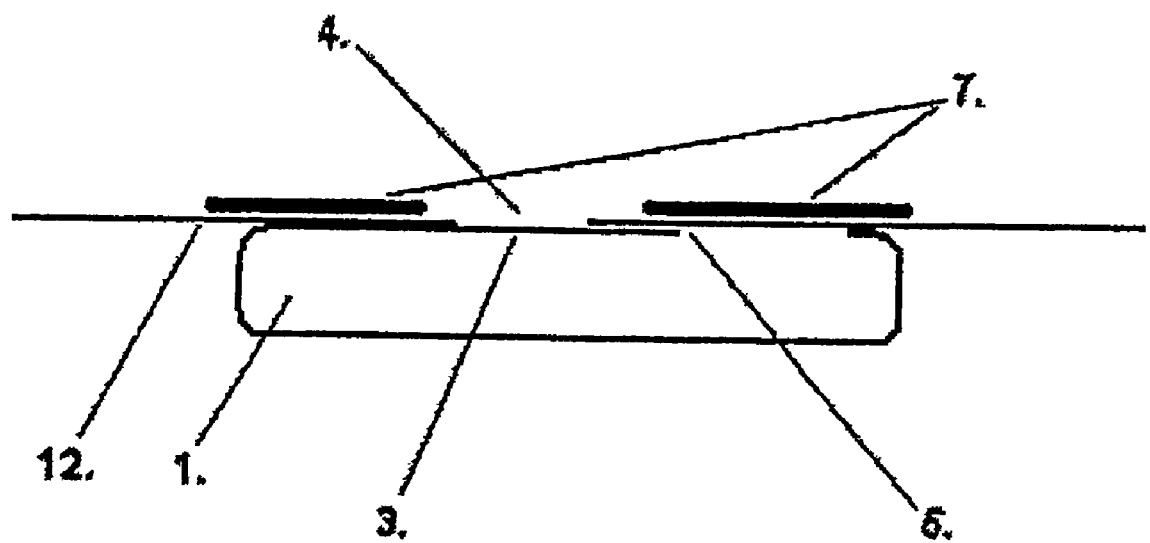
FIG. 4 is a side view of a second alternate embodiment of the device for collection of uncontaminated urine from a child.

According to the second alternate embodiment shown in FIG. 4, the container of the device 1 is attached to the lower side of yet another layer 12. This layer can, for example, be in the form of a diaper, and its main purpose is to function as an alternative attachment device for the container. Said layer 12 has, in this case, been equipped with those details and functions which were placed directly on the upper side of the container in the previous suggestion.

The device comprises a container 1 with sufficient volume to be able to contain the appropriate amount of urine. The container can, for example, be rectangular, oval or anatomically shaped. It can be manufactured from one or several pieces of material. Said container 1 can, for example, be made of a fluid impermeable plastic film made of a thermoplastic material like polyethylene or polypropylene. The container 1 can be welded, glued or otherwise assembled in any other way known to humanity.

The inlet of the container 1 starts with an opening 4 in a layer of plastic material 2 that has been attached to a lower layer 3 so that a tube like channel 5 is formed. These layers can be made from the same work piece as the container, according to the first embodiment (see FIGS. 1-3), or from two different pieces, according to the second alternate embodiment (see FIG. 4).

The opening 4 is situated at the most appropriate place of the device depending on the design and should be designed so that it facilitates the opening of said channel 5. It should be as small as possible because of the risk of contamination, yet large enough to render a correct placement of the device when applied to the body. Said channel 5 can be of different sizes and can be located anywhere within said opening 4.

The aperture of the container consists of said channel 5 which entrance consists of a funnel-shaped flange 6. This flange should be designed so that is leads the fluid towards said channel 5 without preventing the initial part of the fluid from reaching the absorbing layer 7. One possible design is presented in FIGS. 1-3, where the upper plastic layer 2 has been attached 11 to the lower layer 3, so that the flange extends around the opening 4 to its opposite side where the lower layer 3 has been attached to the outer rim of the upper layer 2.

The channel 5 is initially closed in a way that enables it to open automatically, shortly after coming in contact with the fluid. Such a delaying mechanism 9 could be accomplished with a suitable water soluble substance or material that dissolves within a specified time frame. This substance or material can consist of glue, an adhesive polymer or any other known substance or material with preferred characteristics. It should, however, not contain any substances that affect the quality of the sample in any significant way.

On the upper side of the container 1, an absorbing layer 7 is placed close to the opening 4. This material could, e.g. consist of cellulose fibers, viscose fibers or super absorbing synthetic polymers such as polyacrylate. The layer can be designed in any form, for example, round, oval or rectangular, and should be placed where it best serves its function.

It can also be designed according to gender and equipped with anatomically-shaped contour to enhance fitting. The material should be chosen and designed so that a certain amount of fluid is absorbed within a predefined time frame. It can also be surrounded by a waterproof barrier to prevent too much fluid from being absorbed or reach the adhesive surface 8 that attaches the device to the body. This barrier can, for example, be manufactured from a surface treated, non-woven material or from any other suitable material.

The absorbing layer 7 can be covered with a surface layer that only permits fluid to flow in one direction, so that the already absorbed fluid is prevented from leaking back, and thereby reaching the container. This layer can consist of any known appropriate material available on the market, and can, for example, consist of a non-woven material that has been surface treated, laminated or prepared in any other way, and thereby achieve preferred characteristics.

The device can also be provided with one or several adhesive surfaces 8 partly to keep the device in place, partly to prevent leakage. The adhesive surfaces 8 can consist of any waterproof adhesive substance of those commonly used in this context. Especially suitable are those of hydrocolloid or hydrogel type. The surfaces can be of any shape and number, and can be placed anywhere on the device. The surfaces can be supplied with a protective sheet that can be removed before use.

The invention claimed is:

1. A disposable device for collection of an uncontaminated urine sample from a small child, comprising:
   a sterile container adapted to be attached to a uro genital part of the child, an inlet to the container initially closed by a delaying mechanism, the delaying mechanism automatically opening the inlet within a predetermined amount of time after the inlet is reached by urine and thereby preventing a first portion of the urine from reaching the container, the first portion of the urine absorbed by an absorbent material placed around the urine path from the uro genital part to the inlet, and the inlet having a channel for eliminating direct contact between a skin surface of the child and the inside of the container.

2. A disposable device according to claim 1, wherein the delaying mechanism is a water soluble adhesive adapted to dissolve on contact with the urine.

3. A disposable device according to claim 1, wherein the absorbent material is covered by a layer of material adapted to allow the urine to flow through in one direction.

4. A disposable device according to claim 1, wherein the absorbing material is surrounded by a waterproof barrier for preventing over absorption of the area.

5. A disposable device according to claim 1, wherein the absorbing material has an anatomically-shaped contour to fit wearers of both sexes.

6. A disposable device according to claim 1, wherein the device has at least one adhesive surface for securing the device to the uro genital part of the child.

7. A disposable device according to claim 1, wherein the container is attached to a diaper.

8. A disposable device according to claim 1, wherein the inlet to the channel is a funnel-shaped flange.

* * * * *